(12) United States Patent
Barnhart

(10) Patent No.: US 6,413,476 B1
(45) Date of Patent: Jul. 2, 2002

(54) AROMATIC DIFFUSER WITH REPLACEABLE CARTRIDGE

(76) Inventor: Mary F. Barnhart, 284 Hillsboro Rd., Taylorsville, NC (US) 28682

( * ) Notice: Subject to any disclaimer, the term of this patent is extended or adjusted under 35 U.S.C. 154(b) by 0 days.

(21) Appl. No.: 09/286,553

(22) Filed: Apr. 5, 1999

Related U.S. Application Data

(63) Continuation-in-part of application No. 08/984,763, filed on Dec. 4, 1997.
(60) Provisional application No. 60/032,417, filed on Dec. 5, 1996, and provisional application No. 60/058,781, filed on Sep. 12, 1997.

(51) Int. Cl.[7] .................................................. A62B 7/08
(52) U.S. Cl. ........................... 422/124; 422/5; 422/123; 422/125; 422/305
(58) Field of Search ........................... 422/5, 123, 124, 422/125, 305

(56) References Cited

U.S. PATENT DOCUMENTS 3,948,445 A * 4/1976 Andeweg .................... 239/136
5,342,584 A * 8/1994 Fritz et al. .................. 422/124
5,431,885 A * 7/1995 Zlotnik et al. ................ 422/22

* cited by examiner

Primary Examiner—Robert J. Warden, Sr.
Assistant Examiner—Imad Soubra
(74) Attorney, Agent, or Firm—Robert W. Pitts

(57) ABSTRACT

A diffuser for dispersing an aroma into a surrounding area includes a cartridge 100 having an aromatic substance dispersed in a wax carrier 102. The cartridge 100 includes a container 3 in which the wax carrier 102 is located and a cover 2 that includes a central vented tubular projection 27. The container is positioned in a heat conductive cup 6 and a heating element 7 is located below the cup 6 A fan 21 forces air past the cup 6 and aromatic vapors released when the wax carrier 102 is at least partially melted are entrained by the air currents and released through a vented dome 1 at the top of the diffuser. An outer cylindrical housing 12 is used to mount the components. When the heat is removed, the wax carrier solidifies, trapping the aromatic substance. The cartridge vent 27 extends into the container 3 and the annular volume around the inwardly projecting vent is sufficient to provide space for the melted wax if the diffuser is upset.

20 Claims, 6 Drawing Sheets

AROMATIC DIFFUSER WITH REPLACEABLE CARTRIDGE

CROSS REFERENCE TO PRIOR PENDING APPLICATIONS AND PRIOR PROVISIONAL PATENT APPLICATIONS

This application is a continuation in part of prior copending application Ser. No. 08/984,763, filed Dec. 4, 1997, which claimed the benefit of Provisional Application Ser. No. 60/032,417, filed Dec. 5, 1996 and Provisional Application Ser. No. 60/058,781 filed Sep. 12, 1997.

BACKGROUND OF THE INVENTION

1. Field of the Invention

This application is related to a diffuser for dispersing or diffusing an aroma into a surrounding area, and to a replaceable cartridge that can be used with that diffuser. This invention is also related to a diffuser that can be positioned on a table top and which can be easily refilled by inserting a new aromatic cartridge on the top of the diffuser. The cartridge used in this diffuser includes a wax carrier in which an aromatic substance is dispersed, and the cartridge is shaped so that no hot liquids are spilled when the diffuser is upset.

2. Description of the Prior Art

At present there are only relatively ineffective products available to the consumer who wishes to impart a pleasant fragrance to their living and working environments. These products include scented candles, potpourris, carpet powders, wall socket scented plug-in devices and aerosol sprays. These products do not last and are very costly to replace on a continual basis. Only a select group of people are currently aware of a unit called a diffuser that works on electrical power to "diffuse" aromatic scents into the air and would accomplish an effective dispersion of beautiful aromas. Unfortunately, these diff-users are quite expensive and are unavailable to the general public and are very costly to use as they require large amounts of costly fragrance oils to operate.

Plug in products cover only approximately 4–6 square feet and require costly frequent refills and a limited variety of scents are available. Carpet powders are only effective for a 24–48 hour period and can be harmful to the carpeting and are an irritant to infants and pets. Scented aerosol sprays are initially overpowering and their effectiveness quickly deteriorates. They must be continually expelled to achieve desired results and can be irritating and offensive to the user. A limited variety of scents are available. Electric simmering potpourri—crock pots require continual attendance because water must be added. Simmered potpourri chips are unsightly and messy and must be removed and replaced. Similar problems exist with simmering fragrances on a stove. Scented furnace filter pads do not last and must be constantly replaced. They are not recommended for use by most furnace manufacturers because they can clog and obstruct furnace air flow. Aeromatherapy electric aroma devices designed for inhalation are considered a unique medicinal healing art and are not available to the general public. These units are both unattractive and expensive to operate, sometimes requiring ½ oz. of the aromatic oil per day at a cost of $5.00. Scented candles are usually ineffective and costly to purchase on a continual basis and present the attendant problem of an open flame.

Other air freshening units employ absorbent pads or materials for fixing an aromatic liquid in a form in which it can be used with a fan to disperse the aromatic vapors. However, the vapors are continuously emitted from these absorbent pads so the pads are depleted relatively rapidly. Although wax is used for scented candles, scented wax is not employed in air freshening devices or in diffusers, presumably because of complications in handling hot liquid wax. Table top aroma diffusers can be easily upset and the potential for hot wax spills apparently has deterred the use of wax based carriers in prior art units of this type.

SUMMARY OF THE INVENTION

This invention comprises a replenishable aroma and fragrance diffuser for intermittently dispensing a fragrance or aroma into a surrounding area. The diffuser includes an outer vessel having a base for positioning the diffuser on a horizontal surface and an open interior. The vessel is open at the top. The diffuser also includes a fan located on the interior of the outer vessel or housing, and a heating element also located within the outer vessel. A container is located adjacent to the heating element, the container being fabricated from a heat conductive material. A wax member having a composition comprising an aromatic or fragrant substance dispersed within a wax carrier is located within the container. The heater at least partially melts the wax member so that an aroma or fragrance can be emitted upon the application of heat by the heating element and dispersed by air flow generated by the fan. The wax member comprises an aromatic or fragrant substance dispersed within a wax carrier, the aromatic or fragrant substance being releaseable upon the application of sufficient heat to at least partially melt the wax carrier. Solidification of the wax carrier upon the removal of heat traps the aromatic or fragrant substance within the wax carrier to limit dispersion of the aromatic or fragrant substance. The wax member is insertable and removable through the top of the outer vessel so that the aromatic or fragrant substance can be replenished.

The apparatus for diffusing an aroma to a surrounding area also comprises a vessel suitable for positioning in an upright orientation on a horizontal surface, and a heating element located on the interior of the vessel, and a carrier having an aromatic substance dispersed within the carrier. The carrier is solid at room temperature to trap the aromatic substance, and liquefies when heated to release the aromatic substance. The carrier is located within a container. The container is vented to release vapors but traps any liquids when the vessel is tilted to a horizontal orientation, so that hot liquids are not released when the apparatus is upset.

Another aspect of this invention comprises a cartridge for use in the diffuser apparatus for dispersing an aromatic vapor to a surrounding atmosphere. The cartridge comprises a container with a wax carrier in the container. The wax carrier has an aromatic substance dispersed therein and when heated the wax carrier is melted and the aromatic vapors are released by the aromatic substance. The container has a cover extending over its top surface. The cover is peripherally sealed to the container with a tubular projection centrally located in the cover and extending into the container. The tubular projection has an open innermost end to form a vent though which aromatic vapors can be released when the wax carrier is heated. The tubular projection is spaced from a bottom surface of the container. The wax carrier, with the aromatic substance dispersed therein, is confined to a portion of the container below the innermost end of the container when the wax carrier is in a solid state when the cartridge is in an upright orientation. The tubular projection is spaced from outer walls of the container by a distance sufficient to form an annular volume surrounding the tubular projection at least equal to the volume of the wax carrier, including the aromatic substance, so that the wax carrier, when heated and liquified is trapped between the tubular projection and the container when the cartridge is tilted to a horizontal orientation. Therefore the liquid wax will not spill when the diffuser apparatus, with the cartridge therein, is upset.

DETAILED DESCRIPTION OF THE PREFERRED EMBODIMENT

Figure 1:
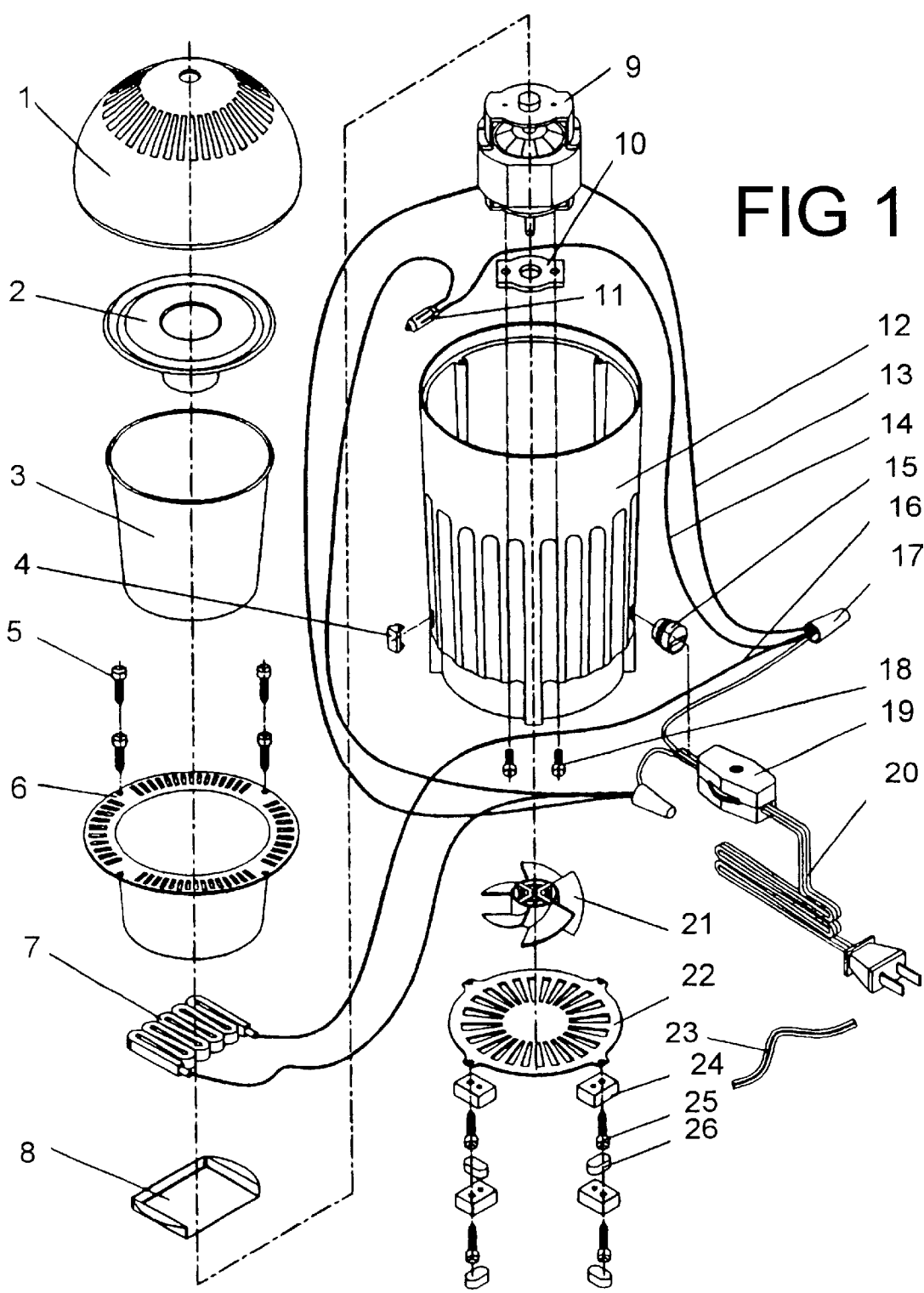
FIG. 1 is an exploded view showing all of the components of the instant invention and the manner in which they can be assembled.
Figure 8:
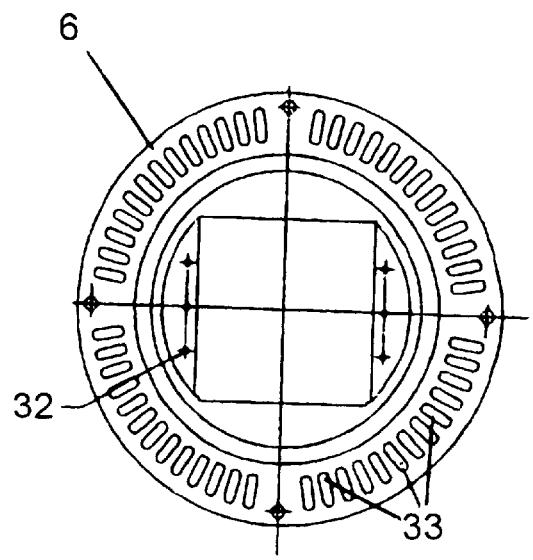
FIG. 8 is a view showing the vents in the top flange of the cup and showing the manner in which the vents extend radially around the cup and the cartridge.
Figure 9:
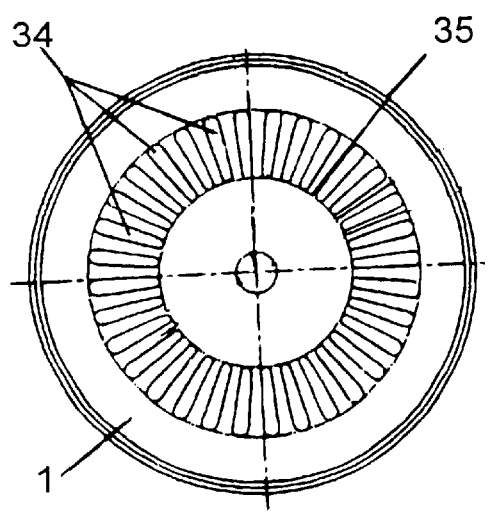
FIG. 9 is a view of the top of the dome or screen and the vented openings that allow aromatic vapors to escape when the wax carrier is heated.
Figure 10:
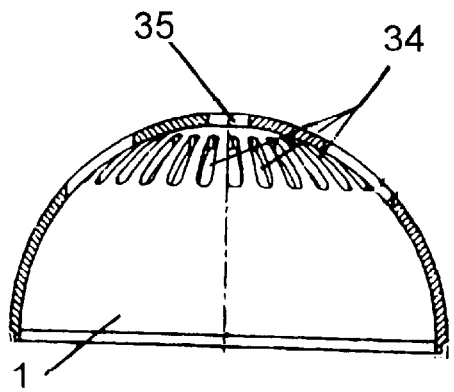
FIG. 10 is a side sectional view of the dome shown in FIG. 9.

The preferred embodiment of this invention comprises a housing or vessel 12 in which a cartridge 100 comprising a wax carrier 102 located in a container 3 is positioned above an electric heating element 7 and a fan 21 powered by an electric motor 9. The housing or vessel 12 serves as the mounting member on which all of the other components are mounted or supported. As shown in FIG. 1, the housing 12 is a cylindrical member, preferably molded from a suitable plastic. The housing 12 is open on the top and bottom and includes a series of axial ridges with holes on the top in which screws 5 can be inserted to mount a cup 6. Cup 6 is formed of a heat conductive material, preferably metal, and includes a central well section with an integral peripheral flange extending radially outward from the central well section. This flange includes four holes that oriented to match the four ridges on the inner wall of the housing 12 so that the screws 5 can be used to attach the cup 6 to the housing 12. The flange includes a series of vented openings 33 shown in FIG. 8 which permit air currents to pass from the lower section of the housing 12 to the upper section, otherwise divided by the cup 6.

A reflector bracket 8 is soldered, welded or otherwise bonded to the bottom wall 32 of the cup 6. This bracket 8 has a rectangular shaped base that is sized to support the electric heating element 7 so that the heating element 7 will be in close proximity to the heat conductive cup 6. As apparent from FIG. 1, the heating element 7 can be inserted into the space between the bracket 8 and the bottom of the cup 6.

Figure 2:
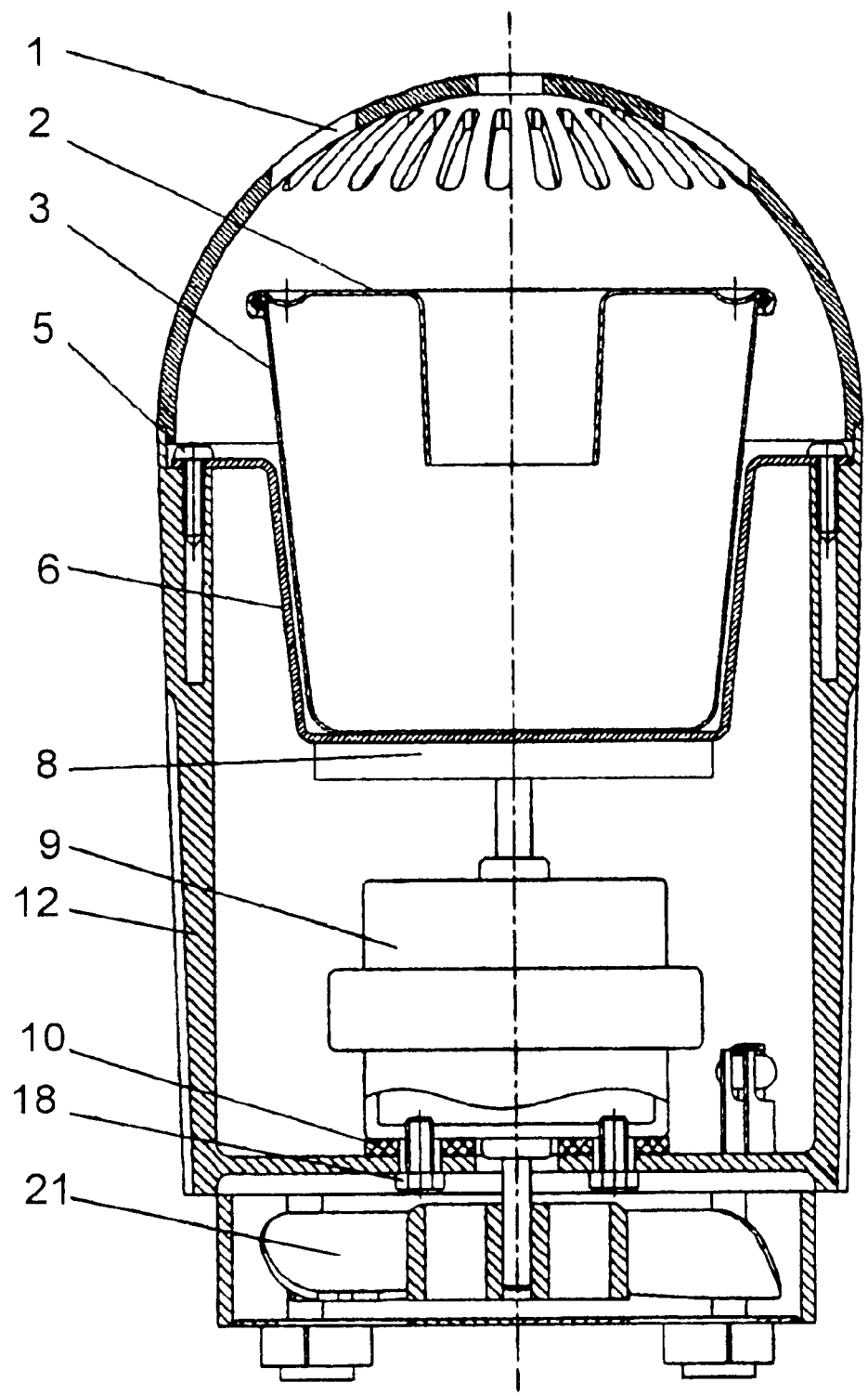
FIG. 2 is a sectional view of the assembled diffuser showing the manner in which the cup, supporting the replaceable cartridge can be mounted in the outer housing or vessel.
Figure 3:
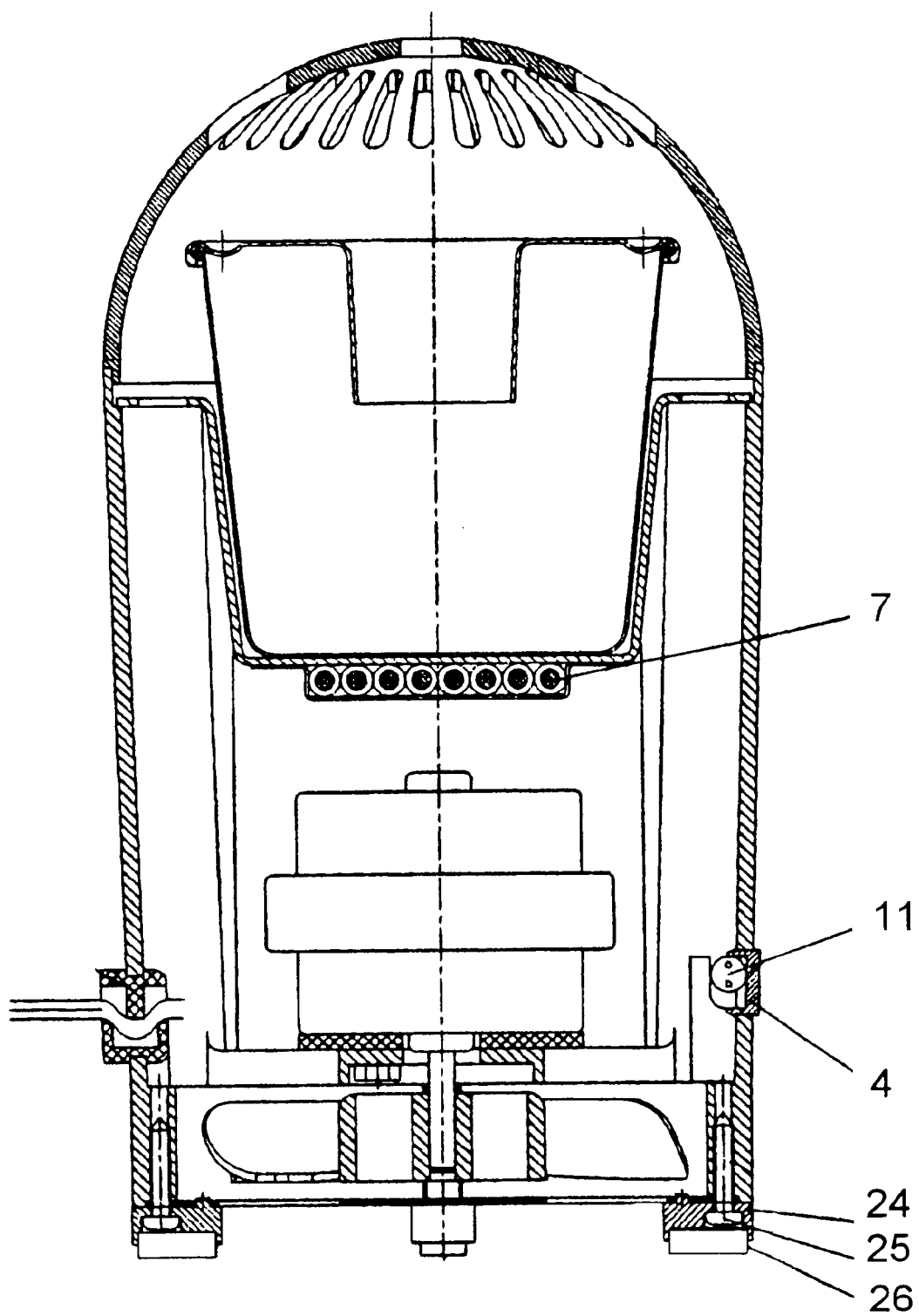
FIG. 3 is a sectional view rotated ninety degrees with respect to FIG. 2 and showing the heater coils.
Figure 4:
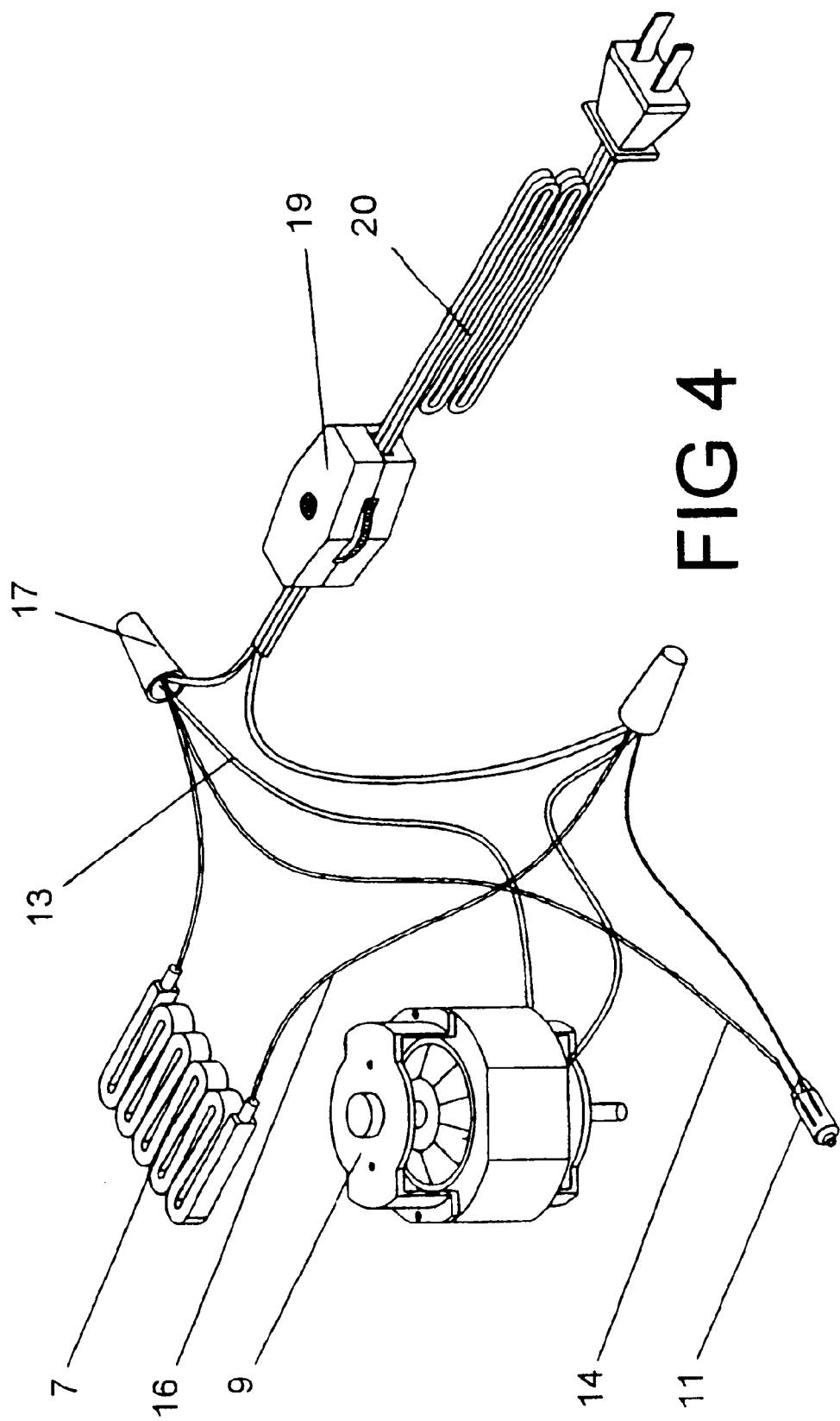
FIG. 4 is a view of the wiring harness including the heater coils and the fan.

The heating element 7 and the fan motor 9 are connected to a wiring harness along with an on-off switch 19 and an electric plug at the end of a power cord 20 as shown in FIGS. 1 and 4. The fan 21 and fan motor 9 are mounted in the bottom section of the housing 12 below the cup 6. The fan 21 is oriented to entrain air at the base of the apparatus and impel the air upward on the inside of the housing 12. This air passes through the vents 33 in the cup flange. A vented grate 22 is attached to the bottom of the housing 12 by screws 25 which pass through foot seats 24. Feet 26 are attached by screws at four corners to support the housing 12 above a horizontal surface, such as a table, on which the apparatus is mounted in an upright orientation with the axis of the housing 12 being substantially vertical. A gap is thus formed between the housing 12 and the supporting horizontal surface so that air my be drawn into the bottom of the apparatus from the outside. As seen in FIG. 2, the fan motor 9 is attached to arms extending radially inwardly form the outer wall of the housing 12 by screws 18. A cushion 10 is located below the fan motor 9 to dampen vibration. As is apparent from FIG. 1, the fan assembly is inserted into the housing 12 from the top, after which the heater subassembly including the heating element 7, the cup 6 and the bracket 8 are subsequently inserted into the housing 12 from the top.

The harness subassembly also includes an indicator light 11 which is mounted near the base of the housing 9. A strain relief 15 secures the power cord 20 which exits at a different angular location. The components of the harness subassembly are connected by wires 13, 14, 16 which are spliced by conventional wire nuts or twist on connectors 17. When the apparatus is fully assembled, the on-off switch 10 and the power cord 20 are located on the exterior of the housing 12 and the power cord is bundled by a standard bundle tie 23.

A semispherical dome 1 is mounted on the top of the housing 12. This dome 1 is preferably molded from a plastic material and includes a central opening 35 surrounded by a series of elongate vent openings 34. The outer rim of the dome 1 fits along a lip at the top of the housing 12. Aromatic vapors are released when the wax carrier 102 is partially melted. These vapors are entrained by air rising upwardly through peripheral openings 33 and the freshly scented air is then passed through openings 34, 35 to the surrounding atmosphere.

Figure 5:
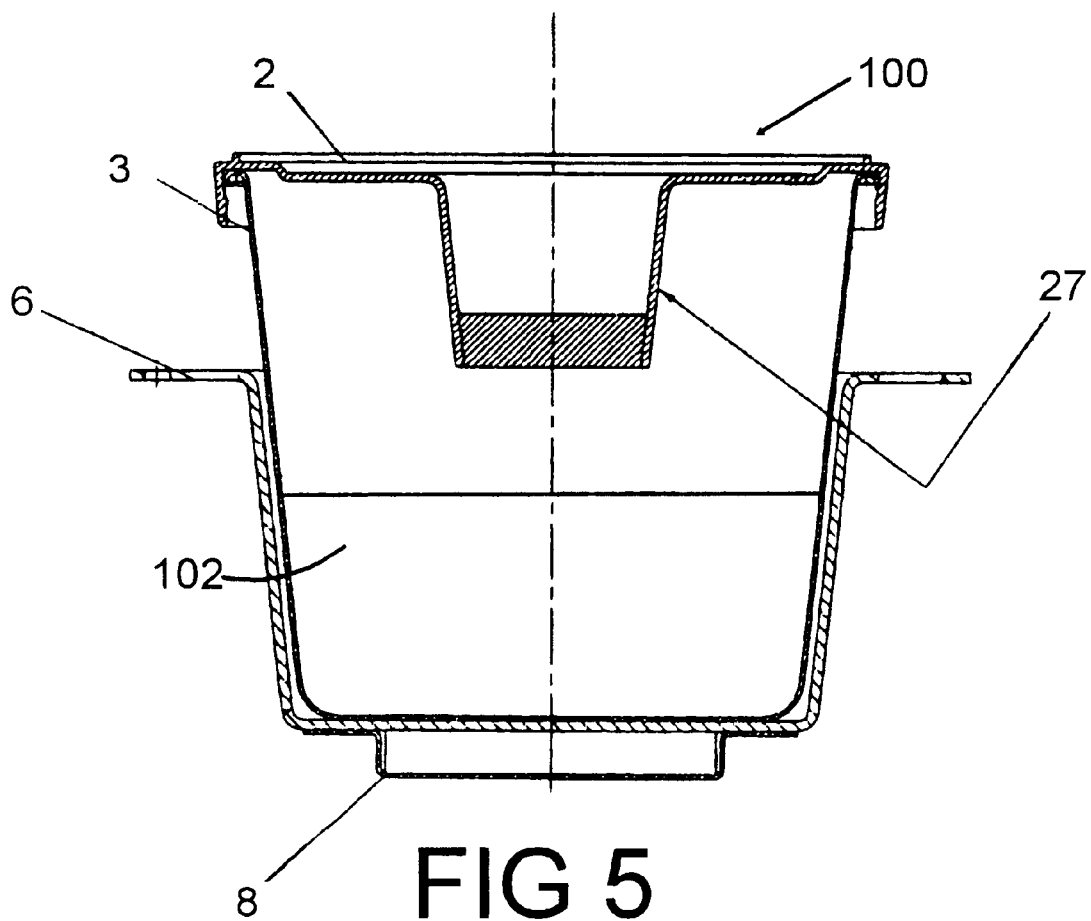
FIG. 5 is a sectional view showing the replaceable cartridge with a centrally located vent projection mounted in the container above the location of the heater coils and showing the relative level of the solid wax carrier.

A replaceable cartridge 100 comprising a wax carrier 102 in which an aromatic substance, such as an aromatic oil is dispersed, a container 3 and a cover 2 secured to the container 3 can be inserted through the top of the housing 12 after removal of dome 1. The container 3 is dimensioned so that the lower portion of the container 3 fits within the cup 6 as shown in FIG. 5. Note that the level of the wax carrier 102 is such that the wax is surrounded on the sides and the bottom by the heat conductive cup 6. Close proximity of the heating element 7 means that the wax carrier can be easily melted when the heating element 7 is activated.

Figure 6:
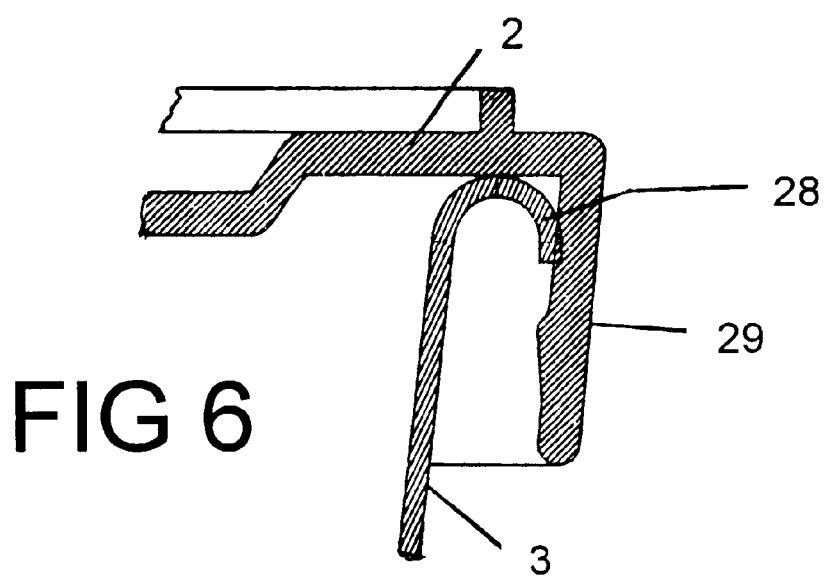
FIG. 6 is a detailed view of the peripheral seal between the container and the cover forming the replaceable cartridge.
Figure 7:
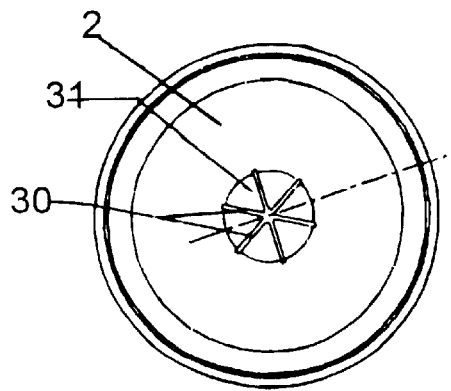
FIG. 7 is a top view of the cartridge cover.

The cover 2 is assembled to the top of the container 3. As shown in FIG. 6 a flange 29 on the cover 2 fits around a radiused lip 28 along the top rim of the container 3 so that a press fit seal is formed around the periphery of the container 3. The cover 2 also includes an inwardly projecting vent or tubular projection 27 at the center of the circular cover. The vent 27 has a frusto-conical shape and is open on the top and bottom. As shown in FIG. 6 and 7, the cover has radially extending strengthening ribs 30 extending across the vent opening 31 at the innermost end of the vent tower 27.

As shown in FIG. 5, the innermost end of the vent 27 is approximately in the same plane as the top of the cup 6 when the cartridge 100 is positioned in the well of the cup 6. The level of the wax carrier is below the innermost or bottom end of the vent 27 and the vent is spaced from the truncated conically shaped sidewalls of the container 3. The annular volume surrounding the central vent or tubular projection 27, between the vent 27 and the side of the container 3, is at least equal to the volume of the wax carrier 102 when the wax carrier, and the aromatic substance disposed therein, is in a liquid state. Thus if the cartridge 100 is turned upside down, the hot liquid wax will reside in this annular area so that wax will not spill. When the cartridge 100 is horizontal, the vent 27 will also be located above the upper surface of the hot liquid wax so that the wax will remain in the cartridge 100.

The wax member 102 can be replenished by replacement of the cartridge 100. When the wax carrier 102 is heated, aromatic or fragrant vapors are released from the wax carrier. When heat is removed, the wax solidifies trapping the remaining aromatic or fragrant substance so that aromatic vapors are either not released or are released at a extremely low rate so that any aroma is not noticeable in the surrounding area and so that the aroma or fragrance is not depleted. In the preferred embodiment of this invention a paraffin wax carrier is used and a fragrant or aromatic liquid is dispersed within the paraffin wax carrier. Conventional fragrant liquids or fragrant oils are dispersed in liquid paraffin wax at a volumetric concentration of approximately one-third. Fragrant liquids are preferred, but aromatherapy oils can also be used. After the oils or liquids are dispersed within the paraffin it is allowed to cool trapping the oils throughout the wax member 102. It has been determined that heating the wax member 102 to a temperature of between one hundred twenty and one hundred thirty degrees Fahrenheit is sufficient to release the aromatic vapors and this temperature will not sufficient to impose any fire or safety hazards. In use the paraffin wax carrier is heated by the heating element 7 to release the fragrant vapors. When the heat is removed, the paraffin wax solidifies and again traps the fragrant liquid so that no vapor is released and the fragrant liquids or oils are not prematurely depleted. When the fragrant oils have been depleted, the cartridge 100 is replaced by removing the container 3 without removing the cover 2 and inserting a new cartridge 100. The dome 1 is removable to permit replacement of the cartridge 100 from above. The used cartridge 100 can then be discarded.

I claim:

1. A replenishable aroma and fragrance diffuser for intermittently dispensing a fragrance or aroma into a surrounding area comprising:
    an outer vessel having a base for positioning the diffuser on a horizontal surface and an open interior, the vessel being open at the top;
    a fan located on the interior of the outer vessel;
    a heating element located within the outer vessel;
    a container located adjacent to the heating element, the container being fabricated from a heat conductive material and comprising means for holding a heated liquid but releasing an aroma from the heated liquid; and
    a wax member having a composition comprising an aromatic or fragrant substance dispersed within a wax carrier, the wax composition being disposed within the container, the heater at least partially melting the wax member so that an aroma or fragrance can be emitted upon the application of heat by the heating element and dispersed by air flow generated by the fan, wherein the aromatic or fragrant substance is releaseable upon the application of sufficient heat to at least partially melt the wax carrier, solidification of the wax carrier upon the removal of heat trapping the aromatic or fragrant substance within the wax carrier to limit dispersion of the aromatic or fragrant substance;
    the wax member and the container being insertable and removable through the top of the outer vessel so that the aromatic or fragrant substance can be replenished by replacing the container wherein the container has venting openings to release vapors but the container is shaped to have sufficient volume between sides of the container and the vented openings to trap any liquids when the vessel is titled to a horizontal orientation, so that hot liquids are not released through the venting openings when the apparatus is inadvertently tilted from an upright orientation to a horizontal orientation.

2. The diffuser of claim 1 wherein the fan and the heating element are located below the wax member.

3. The diffuser of claim 1 wherein the container and the wax member are disposable and replaceable through the top of the outer vessel.

4. The diffuser of claim 1 wherein a vented top dome is located on the top of the outer vessel, the vented top dome being removable to permit insertion and removal of the wax member.

5. The diffuser of claim 1 wherein the aromatic or fragrant substance is dispersed within the wax carrier in a concentration of approximately ten percent of the volume of the wax member.

6. The diffuser of claim 1 wherein the wax member includes a wax carrier comprising a paraffin wax.

7. The diffuser of claim 1 wherein the outer vessel includes means for positioning the fan adjacent to the outer vessel base and for supporting the heating element above the fan and for supporting the container above the heating element.

8. An apparatus for diffusing an aroma to a surrounding area comprising:
    a vessel suitable for positioning in an upright orientation on a horizontal surface;
    a heating element located on the interior of the vessel; and
    a carrier having an aromatic substance dispersed within the carrier, the carrier being solid at room temperature to trap the aromatic substance, and liquefying when heated to release the aromatic substance, the carrier being disposed within a cartridge, the cartridge having venting openings to. release vapors but the cartridge being shaped to have sufficient volume between sides of the cartridge and the vented openings to trap any liquids when the vessel is tilted to a horizontal orientation, so that hot liquids are not released through the venting openings when the apparatus is inadvertently tilted from an upright orientation to a horizontal orientation.

9. The apparatus of claim 8 wherein the cartridge is vented to trap any liquids when the vessel is tilted form an upright orientation to an upside down orientation.

10. The apparatus of claim 8 wherein the cartridge includes a bottom container forming a cavity in which the carrier is located with a cover positioned over an open upper end of the container, the cover including a vent for releasing vapors from the aromatic substance.

11. The apparatus of claim 10 wherein the vent is located in the center of the cover.

12. The apparatus of claim 11 wherein a tubular extension is located in the center of the cover projecting centrally into the container, the tubular extension being open at its innermost end to form the vent.

13. The apparatus of claim 12 wherein the volume in the container surrounding the tubular extension is at least equal to the volume of the carrier when the carrier is in a liquid state.

14. The apparatus of claim 13 wherein the volume surrounding the tubular extension comprises an annular volume.

15. The apparatus of claim 12 wherein the container has a continuous side surface with a truncated conical shape.

16. The apparatus of claim 8 wherein the carrier comprises a wax with an aromatic liquid substance dispersed in the wax when the wax is in a solid state.

17. The apparatus of claim 8 wherein a cup is mounted in the vessel adjacent the heating element, the cup forming a cavity in which the cartridge container is positioned.

18. The apparatus of claim 8 wherein the cup extends above an upper surface of the wax carrier when the cartridge container is positioned in the cup.

19. The apparatus of claim 18 wherein the cup includes peripheral vents between the housing and a cartridge container positioned in the cup, and a fan mounted below the cup forces fresh air up through the vents to entrain aromatic vapors released when the wax carrier is heated.

20. A cartridge for use in a diffuser apparatus for dispersing an aromatic vapor to a surrounding atmosphere when the cartridge is heated, the cartridge comprising:

a container with a wax carrier in the container, the wax carrier having an aromatic substance dispersed therein:

a cover extending over a top surface of the container, the cover being peripherally sealed to the container with a tubular projection centrally located in the cover and extending into the container, the tubular projection having an open innermost end to form a vent though which aromatic vapors can be released when the wax carrier is heated, the innermost end of the tubular projection being spaced from a bottom surface of the container and from the wax carrier, the wax carrier with the aromatic substance dispersed therein being confined to a portion of the container below the innermost end of the tubular projection, when the wax carrier is in a solid state and the cartridge is in an upright orientation, the tubular projection being spaced from outer walls of the container by a distance sufficient to form an annular volume surrounding the tubular projection at least equal to the volume of the wax carrier; including the aromatic substance, so that the wax carrier, when heated and liquified is trapped between the tubular projection and the container when the cartridge is tilted to a horizontal orientation, so that liquid wax will not spill when the diffuser apparatus, with the cartridge therein, is upset.

* * * * *